United States Patent
Iwase et al.

(10) Patent No.: US 9,814,487 B2
(45) Date of Patent: Nov. 14, 2017

(54) METHOD FOR MANUFACTURING PUNCTURE NEEDLE AND PUNCTURE NEEDLE

(71) Applicant: NIPRO CORPORATION, Osaka (JP)

(72) Inventors: Yoshiharu Iwase, Tatebayashi (JP); Yutaka Eizumi, Tatebayashi (JP); Kenji Kurokawa, Tatebayashi (JP)

(73) Assignee: NIPRO CORPORATION, Osaka-shi, Osaka (JP)

( * ) Notice: Subject to any disclaimer, the term of this patent is extended or adjusted under 35 U.S.C. 154(b) by 815 days.

(21) Appl. No.: 14/361,197

(22) PCT Filed: Nov. 30, 2012

(86) PCT No.: PCT/JP2012/081063
§ 371 (c)(1),
(2) Date: May 28, 2014

(87) PCT Pub. No.: WO2013/084814
PCT Pub. Date: Jun. 13, 2013

(65) Prior Publication Data
US 2014/0336687 A1 Nov. 13, 2014

(30) Foreign Application Priority Data
Dec. 5, 2011 (JP) .................... 2011-266293

(51) Int. Cl.
*B24B 19/00* (2006.01)
*A61B 17/34* (2006.01)
(Continued)

(52) U.S. Cl.
CPC ...... *A61B 17/3417* (2013.01); *A61B 10/0233* (2013.01); *B24B 19/009* (2013.01);
(Continued)

(58) Field of Classification Search
CPC .... B24B 19/009; B24B 19/022; B24B 19/028
(Continued)

(56) References Cited

U.S. PATENT DOCUMENTS 2,420,504 A * 5/1947 Stewart ................ B24B 19/022
125/11.16
6,149,501 A * 11/2000 Farzin-Nia ............... A61O 5/42
451/48
(Continued)

FOREIGN PATENT DOCUMENTS

| JP | 2006-101915 A | 4/2006 |
|---|---|---|
| JP | 2010-194013 A | 9/2010 |
| JP | 2011-125632 A | 6/2011 |

OTHER PUBLICATIONS

International Search Report for PCT/JP2012/081063 (1 page).

*Primary Examiner* — George Nguyen
(74) *Attorney, Agent, or Firm* — Flynn, Thiel, Boutell & Tanis, P.C.

(57) ABSTRACT

A puncture needle includes a needle tube 1 provided with a spiral groove 3 and wall surfaces 3a and 3b of the spiral groove 3 serve as a surface for reflecting ultrasonic waves. The spiral groove is formed on the peripheral surface of the needle tube such that a grinding stone 2 is brought into contact with the peripheral surface of the needle tube while the needle tube 1 is being moved in its axial direction and rotated.

The wall surfaces of the spiral groove formed on the needle tube serve as a reflection surface to change the orientation of the reflection surface in the axial direction of the needle tube according to change in position of the spiral. Therefore, even if a direction in which an ultrasonic wave is applied to the puncture needle is fixed, any portion of the reflection surface changing in orientation can become a surface for reflecting well ultrasonic waves, so that good ultrasonic waves can be (Continued)

obtained. The slant angles of the reflection surfaces in the axial direction of the needle tube can be changed by adjusting the moving speed in the axial direction of the needle tube or the rotation speed.

3 Claims, 2 Drawing Sheets

(51) Int. Cl.
  *A61B 10/02* (2006.01)
  *B24B 19/02* (2006.01)
  *A61B 8/08* (2006.01)
  *A61B 17/00* (2006.01)
  *A61B 90/00* (2016.01)

(52) U.S. Cl.
  CPC ............ *B24B 19/02* (2013.01); *B24B 19/022* (2013.01); *B24B 19/028* (2013.01); *A61B 8/0841* (2013.01); *A61B 2017/00526* (2013.01); *A61B 2090/3925* (2016.02)

(58) Field of Classification Search
  USPC ...................................................... 451/28, 51
  See application file for complete search history.

(56) References Cited

U.S. PATENT DOCUMENTS

| | | | | |
|---|---|---|---|---|
| 2004/0101379 A1* | 5/2004 | Mabuchi | ................. | B23B 51/02 |
| | | | | 408/230 |
| 2006/0014480 A1* | 1/2006 | Aloise | .................... | B21F 99/00 |
| | | | | 451/149 |

\* cited by examiner

METHOD FOR MANUFACTURING PUNCTURE NEEDLE AND PUNCTURE NEEDLE

TECHNICAL FIELD

The present invention relates to a method for manufacturing a puncture needle whose tube is provided with a surface for reflecting ultrasonic waves and the puncture needle manufactured by the manufacturing method.

BACKGROUND ART

Up to now, a puncture needle whose needle tube is provided with a surface for reflecting ultrasonic waves has been already known. Patent Literature 1 discusses examples in which a large number of dotted depressions are formed on the surface of the needle tube so that the wall surface of each depression is used as a reflection surface and a large number of circular grooves are formed so that the wall surface thereof is used as a reflection surface.

Patent Literature 1 also discusses methods for forming the reflection surface in which a rod-shaped cutter is rotated and the leading edge thereof is obliquely pressed against the surface of the needle tube or an electric discharge machining or a laser machining is used.

PRIOR ART DOCUMENTS

Patent Literature

Patent Literature 1: Japanese Patent Laid-Open No. 2010-194013

SUMMARY OF INVENTION

Problems to be Solved by the Invention

The dotted depressions and a large number of circular grooves formed on the surface of the needle tube contribute toward providing a good ultrasonic echo, however, the puncture needle needs to be inserted into the skin at a predetermined angle with respect to ultrasonic waves applied in a certain direction to reflect well ultrasonic waves. At the same time, a practitioner who uses the puncture needle desires the puncture needle capable of more easily providing a good ultrasonic echo.

The method for forming the dotted depression using the rod-shaped cutter is not suited for mass production because it takes much time for the method to form the dotted depression and a slant angle of the cutter with respect to the needle tube needs to be changed in each case, particularly when forming reflection surfaces each different in slant angle.

On the other hand, the method for forming the dotted depression using the electric discharge machining or the laser machining is also not suited for mass production because it takes much time for the method to accurately form reflection surfaces each different in slant angle.

In view of such situations, the present invention has been made to provide a method for manufacturing a puncture needle capable of manufacturing the puncture needle including a reflection surface more easily providing a good ultrasonic echo at a low cost and on a mass-production basis and the puncture needle including the reflection surface providing a good ultrasonic echo manufactured by the manufacturing method.

Means for Solving the Problems

According to claim 1 of the present invention, a method for manufacturing a puncture needle of which a needle tube is provided with a surface for reflecting ultrasonic waves includes bringing a grinding stone into contact with the peripheral surface of the needle tube while the needle tube is being moved in its axial direction and rotated to cause the grinding stone to form a spiral groove on the peripheral surface of the needle tube, forming the wall surfaces of the spiral groove as the reflection surface.

In a puncture needle according to claim 4 of the invention, the puncture needle includes a needle tube provided with a surface for reflecting ultrasonic waves, in which a spiral groove is formed on the needle tube and the wall surfaces of the spiral groove serve as the reflection surface.

Advantageous Effects of Invention

According to a method for manufacturing a puncture needle in claim 1 of the present invention, a grinding stone is brought into contact with the peripheral surface of the needle tube while the needle tube is being moved in its axial direction and rotated to form a spiral groove and the wall surfaces of the spiral groove are used as a reflection surface, so that a groove can be spirally formed on the surface outside the needle tube only by bringing the grinding stone into contact with the needle tube and moving forward the needle tube while the needle tube is being rotated. For this reason, the puncture needle of which the needle tube is provided with a surface for reflecting ultrasonic waves can be manufactured at a low cost and on a mass-production basis.

In the above manufacturing method, the slant angles of the reflection surfaces in the axial direction of the needle tube can be changed by adjusting the moving speed in the axial direction of the needle tube or the rotation speed, so that the reflection surfaces with required slant angles can be easily formed by the adjustment and the reflection surfaces with a plurality of different slant angles can be easily obtained.

In the puncture needle according to claim 4 of the present invention, the spirally formed groove forms surfaces having various orientations depending on the position of the spiral when the needle is slanted. For this reason, even if the puncture needle is inserted without considering so much an angle at which the puncture needle is inserted into the skin, any of the wall surfaces well reflects ultrasonic waves to enable a good ultrasonic echo to be obtained.

MODE FOR CARRYING OUT THE INVENTION

Figure 1:
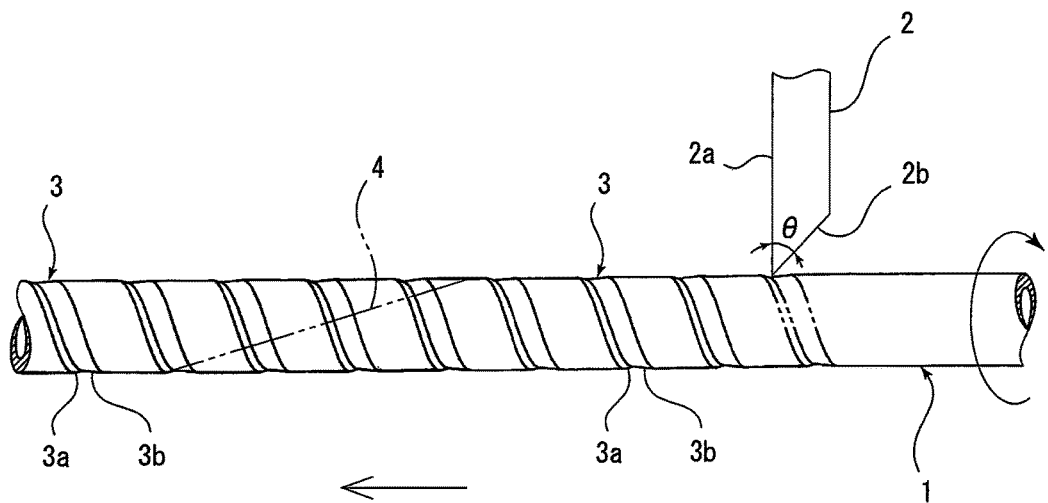
FIG. 1 is a side view of a manufacturing method according to the present invention.

An embodiment of the present invention is described below with reference to the attached drawings. In FIG. 1, a cylindrical needle tube 1 for producing a puncture needle is moved in the axial direction thereof while being rotated with the center axis as a rotation center.

A tool (not shown) for rotating the needle with the needle grasped is provided to move the needle tube 1 in the axial direction while the needle tube 1 being rotated and the tool is reciprocated by a predetermined distance while being rotated. When the needle tube 1 is fixed to the tool and rotated forward by the predetermined distance, the needle tube 1 is released from the tool's grasp and only the tool is moved backward by the predetermined distance with the needle tube 1 left. When the tool again grasps the needle tube 1, the needle tube 1 is rotated forward while being rotated.

A grinding stone 2 is provided at one side portion of the needle tube 1 in the direction in which it is conveyed. The peripheral surface of the grinding stone 2 is brought into contact with the peripheral surface of the needle tube 1 that is moved in the axial direction while being rotated to allow a spiral groove 3 to be formed on the peripheral surface of the needle tube 1.

The grinding stone 2 is formed in a disk shape as a whole and rotationally driven by a driving source (not shown) with the center of the disk-shaped wheel as a rotation center. A shape which is a peripheral-surface shape of the grinding stone 2 is triangular in cross section in the embodiment shown in the figure and is formed such that a surface 2a on the front side in the direction in which the needle tube 1 is conveyed is perpendicular to the axial direction of the needle tube 1.

On the other hand, a surface 2b on the back side in the direction in which the needle tube 1 is conveyed in the peripheral shape of the grinding stone 2 is formed at a slant such that the surface 2b can be slanted against the axial direction of the needle tube 1. The angle is set to be 48.8° in the embodiment shown in the figure. That is, an opening angle θ of the shape of the triangle in cross section is set to be 41.2°.

Figure 2:
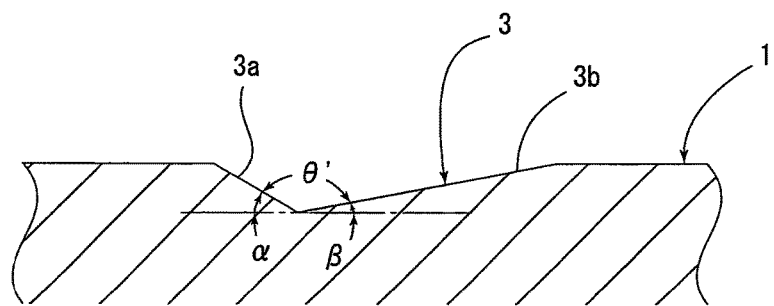
FIG. 2 is an enlarged cross section of the principal part of FIG. 1.

The spiral groove 3 formed by the grinding stone 2 whose the peripheral shape is triangular in cross section becomes triangular in cross section as illustrated by an enlarged view in FIG. 2.

Since the needle tube 1 is moved in the axial direction while being rotated, the cross-sectional shape of the spiral groove 3 does not correspond to the peripheral shape of the grinding stone 2. An opening angle θ' of the spiral groove 3 is larger than the opening angle θ of the grinding stone. Wall surfaces 3a and 3b of the spiral groove 3 on the front and back sides in the direction in which the needle tube 1 is conveyed are slanted oppositely to each other against the axial direction of the needle tube 1 respectively. A slant angle α of the wall surface 3a on the front side in the direction in which the needle tube 1 is conveyed is larger than a slant angle β of the wall surface 3b on the back side.

The wall surfaces 3a and 3b of the spiral groove 3 serve as surfaces for reflecting ultrasonic waves to be applied. The slant angle α of the wall surface 3a on the front side in the direction in which the needle tube 1 is conveyed can be adjusted by the speed of moving the needle tube 1 and set to be 60° or so, for example.

As described above, after the spiral groove 3 is formed on the periphery of the needle tube 1, a glass bead is applied to angle portions formed at both edges of the wall surfaces on the formed spiral groove 3 to round the angle portions.

As is the case with a conventionally known method for manufacturing a puncture needle, the needle tube 1 is cut to a required length. Thereafter, as shown by an imaginary line in FIG. 1, a needle tip 4 is formed on the cut needle tube 1 and the puncture needle is completed.

The needle tip 4 is formed on the front side in the direction in which the needle tube 1 is conveyed and the back side in the direction in which the needle tube 1 is set to a needle root of the puncture needle. Thus, the needle tip 4 is formed on the front side in the direction in which the needle tube 1 is conveyed to orient the wall surface 3a large in a slant angle α on the front side in the conveyance direction toward the needle root. A user generally inserts the needle at a slant under the skin of a patient, the wall surface 3a becomes a surface for reflecting well applied ultrasonic waves, so that the thus formed needle can provide a good ultrasonic echo.

Figure 3:
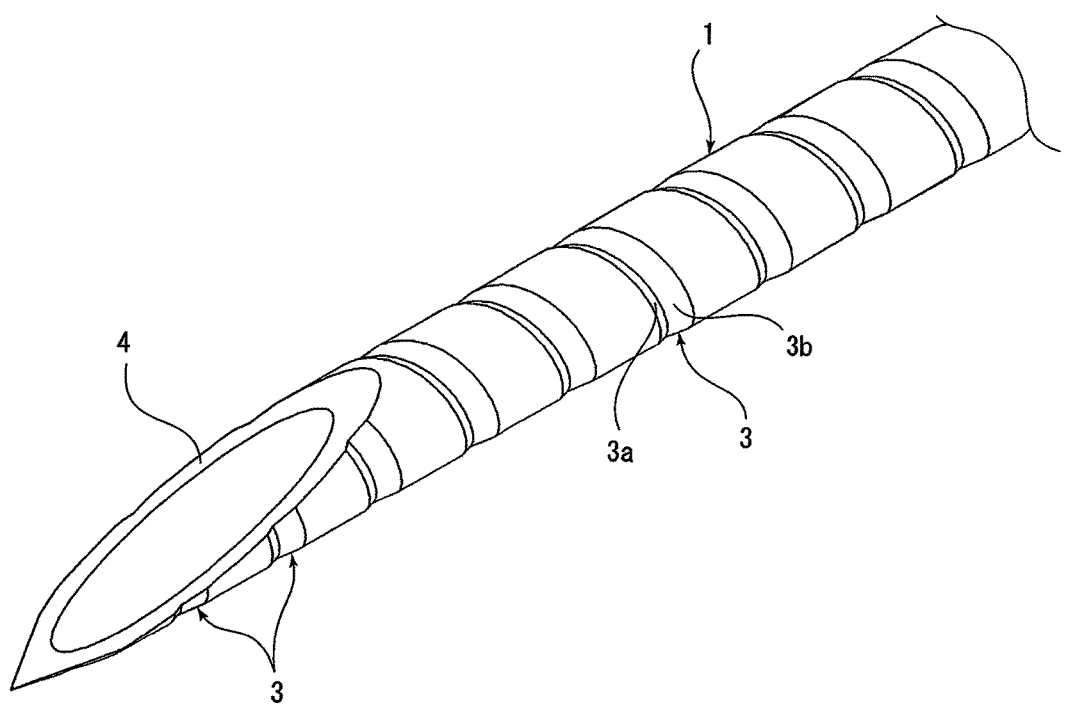
FIG. 3 is a perspective view of a needle-tip portion of the completed puncture needle.

FIG. 3 is a perspective view of the needle tip 4 of the completed puncture needle. The wall surfaces 3a and 3b of the spiral groove 3 formed on the needle tube 1, particularly, the wall surface 3a facing the needle root serves as a good surface for reflecting ultrasonic waves.

The orientation of the wall surfaces 3a and 3b continuously changes according to change in position along the spiral groove 3, so that, even if a direction in which an ultrasonic wave is applied to the puncture needle is constant, any portion of the reflection surface changing in orientation can become a surface for reflecting well ultrasonic waves.

That is, any point of the wall surfaces 3a and 3b can be used as a good surface for reflecting ultrasonic waves irrespective of the direction of the ultrasonic wave, so that a better ultrasonic echo can always be obtained, as compared with the conventional needle. If the spiral groove 3 whose pitch is equal is formed, the good reflection surface appears with an equal pitch in the axial direction of the needle tube 1, so that the user can easily recognize the direction in which the needle is inserted under the skin.

As is clear from the manufacturing method described above, the needle tip 4 is formed after the spiral groove 3 is formed on the needle tube 1, so that the spiral groove 3 is formed also on the back of the needle tip 4 and therefore the needle tip 4 can also provide a good ultrasonic echo.

The glass bead is applied to both ends of the wall surfaces of the spiral groove 3 to flatten and round the angle portions on both ends of the wall surfaces, allowing increase in puncture resistance by the groove formed on the surface of the needle tube to be reduced.

According to the above manufacturing method, the spiral groove 3 is formed using the grinding stone 2 to allow easily forming a groove provided with a favorable deepness and stably obtaining a highly accurate groove shape. For this reason, a puncture needle of which the needle tube is provided with a surface for reflecting well ultrasonic waves can be manufactured at a low cost and on a mass-production basis.

Even if the grinding stone 2 with a single shape shown in FIG. 1 is used, or, if the shape of the grinding stone 2 is fixed, the slant angles α and β of the wall surfaces 3a and 3b of the spiral groove 3 can be adjusted only by adjusting the moving speed in the axial direction of the needle tube 1 or the rotation speed.

More specifically, the moving speed in the axial direction of the needle tube 1 is made higher, as compared with the case described above, to allow the pitch of the spiral groove 3 to be increased and the slant angles α and β of the wall surfaces 3a and 3b to be decreased. On the other hand, the moving speed in the axial direction of the needle tube 1 is made lower to allow the pitch of the spiral groove 3 to be decreased and the slant angles α and β of the wall surfaces 3a and 3b to be increased.

Furthermore, the rotation speed of the needle tube 1 is made higher to allow the pitch of the spiral groove 3 to be decreased and the slant angles α and β of the wall surfaces 3a and 3b to be increased. On the other hand, the rotation speed of the needle tube 1 is made lower to allow the pitch of the spiral groove 3 to be increased and the slant angles α and β of the wall surfaces 3a and 3b to be decreased.

Thus, in the present embodiment, the spiral groove 3 having the wall surfaces 3a and 3b with required slant angles α and β respectively can be easily produced by properly setting the moving speed or the rotation speed of the needle tube 1.

Furthermore, the moving speed or the rotation speed of the needle tube 1 is changed in the process for forming the spiral groove 3 in the needle tube 1 to enable easily producing the puncture needle including the wall surface 3a of which the slant angle α is large on the side of the needle tip 4 or the wall surface 3a of which the slant angle α is small on the side of the needle root or the puncture needle with a slant angle opposite to the above, for example.

In the present embodiment, the grinding stone formed such that the opening angle θ of the shape is 41.2°, the surface 2a on the front side in the direction in which the needle tube 1 is conveyed is perpendicular to the axial direction of the needle tube 1, and the surface 2b on the back side in the direction in which the needle tube 1 is conveyed is slanted against the axial direction of the needle tube 1 is used as the grinding stone 2, however, the present invention is not limited to the above grinding stone. The opening angle θ may be 45°, 30°, 60°, or other angles. It is to be understood that the form of the surfaces 2a and 2b is not limited to the above-mentioned form but a proper form may be selected if needed.

REFERENCE SIGNS LIST

1 Needle tube
2 Grinding stone
2a, 2b Surface
3 Spiral groove
3a, 3b Wall surface
4 Needle tip
θ, θ' Opening angle
α, β' Slant angle

The invention claimed is:

1. A method for manufacturing a puncture needle of which a needle tube includes a surface for reflecting ultrasonic waves, the method comprising:

bringing a grinding stone into contact with the peripheral surface of the needle tube while the needle tube is being moved in its axial direction and rotated to cause the grinding stone to form a spiral groove on the peripheral surface of the needle tube, forming the wall surfaces of the spiral groove as the reflection surface.

2. The method for manufacturing the puncture needle according to claim 1, wherein at least any one of the moving speed and the rotation speed of the needle tube is changed within a range in which one puncture needle is produced, thereby to provide the wall surfaces of the spiral groove with different slant angles in the axial direction of the needle tube.

3. The method for manufacturing the puncture needle according to claim 1, wherein the shape of the grinding stone is formed to be triangular in cross section and the grinding stone is brought into contact with the peripheral surface of the needle tube while the needle tube is being moved in its axial direction and rotated to cause the grinding stone to form a spiral groove which is of V shape in cross section and has an opening angle larger than the opening angle of the grinding stone on the peripheral surface of the needle tube, forming the wall surfaces of the spiral groove as the reflection surface.

* * * * *